(12) United States Patent  
Heslet et al.

(10) Patent No.: US 10,716,831 B2  
(45) Date of Patent: Jul. 21, 2020

(54) METHODS FOR INHIBITING INFECTIOUS PERITONITIS

(71) Applicant: Reponex Pharmaceuticals ApS, Hørsholm (DK)

(72) Inventors: Lars Heslet, Gentofte (DK); Lars Otto Uttenthal, Salamanca (ES)

(73) Assignee: REPONEX PHARMACEUTICALS A/S, Hørsholm (DK)

( * ) Notice: Subject to any disclaimer, the term of this patent is extended or adjusted under 35 U.S.C. 154(b) by 0 days.

(21) Appl. No.: 16/164,669

(22) Filed: Oct. 18, 2018

(65) Prior Publication Data

US 2019/0275107 A1    Sep. 12, 2019

Related U.S. Application Data

(62) Division of application No. 15/502,118, filed as application No. PCT/EP2015/068269 on Aug. 7, 2015, now abandoned.

(30) Foreign Application Priority Data

Aug. 7, 2014 (DK) .................................. 201470473

(51) Int. Cl.
| | | |
|---|---|---|
| *A61K 38/19* | (2006.01) | |
| *A61K 9/00* | (2006.01) | |
| *A61K 31/4164* | (2006.01) | |
| *A61K 31/665* | (2006.01) | |

(52) U.S. Cl.
CPC .......... *A61K 38/193* (2013.01); *A61K 9/0019* (2013.01); *A61K 31/4164* (2013.01); *A61K 31/665* (2013.01)

(58) Field of Classification Search
None
See application file for complete search history.

(56) References Cited

FOREIGN PATENT DOCUMENTS

| WO | WO 00/40269 A2 | 7/2000 |
| WO | WO 2015/118069 A1 | 8/2015 |
| WO | WO 2015/132392 A1 | 9/2015 |

OTHER PUBLICATIONS

Chalkiadakis et al. Effect of aprotinin on fibrinopurulent peritonitis in rats. Am. J. of surgery, 150, 550-3, 1985. (Year: 1985).*
Recombinant human GM-CSF protein 215-GM-010 R&D Systems. retrieved from: https://rndsystems.com/products/recombinant-human gm-csf-protein_215-gm#product-datasheets. (Year: 2019).*
Fosfomycin. retrieved from: https://pubchem.ncbi.nlm.nih.gov/compound/Fosfomycin. (Year: 2019).*
Metronidazole. retrieved from: https://www.scbt.com/p/metronidazole-443-48-1. (Year: 2019).*
McCormack et al. Caspofungin—A review of its use in treatment of fungal infections. Drugs, 65, 2049-2068, 2005. (Year: 2005).*
Austin, O.M.B., et al., The Beneficial Effects of Immunostimulation in Posttraumatic Sepsis, Journal of Surgical Research, vol. 59, pp. 446-449, 1995.
Corso, V. et al., "Immunomodulation with granulocyte-macrophage colony-stimulating factor and interleukin 2 in an experimental model of sepsis" British Journal of Surgery, Jul. 2000, pp. 931-964, vol. 87.
Michel, C. et al., "Treatment of peritonitis in continuous ambulatory peritoneal dialysis with a combination of fosfomycin and pefloxacin" Pathologie-Biologie, Apr. 1989, pp. 269-271, vol. 37, No. 4.
Orozco, Héctor et al., "Molgramostim (GM-CSF) Associated With Antibiotic Treatment in Nontraumatic Abdominal Sepsis" Archives of Surgery, Feb. 2006, pp. 150-153, vol. 141.
Pachón-Ibáñez, M. E. et al., "Efficacy of fosfomycin and its combination with linezolid, vancomycin and imipenem in an experimental peritonitis model caused by a *Staphylococcus aureus* strain with reduced susceptibility to vancomycin" European Journal of Clinical Microbiology & Infectious Diseases, 2011, pp. 89-95, vol. 30.
Spight, Donn et al., "GM-CSF-dependent peritoneal macrophage responses determine survival in experimentally induced peritonitis and sepsis in mice" Shock, Oct. 2008, pp. 434-442, vol. 30, No. 4.
Tobudic, Selma et al., "Pharmacokinetics of Intraperitoneal and Intravenous Fosfomycin in Automated Peritoneal Dialysis Patients without Peritonitis" Antimicrobial Agents and Chemotherapy, Jul. 2012, pp. 3992-3995, vol. 56, No. 7.
International Search Report for PCT/EP2015/068269 dated Oct. 7, 2015.
Ariza, et al.,"Vancomycin in surgical infections due to methicillin-resistant *Staphylococcus aureus* with heterogeneous resistance to vancomycin." Lancet. May 8, 1999;353(9164):1587-8.
Eckmann, et al., "Antimicrobial treatment of "complicated" intra-abdominal infections and the new IDSA guidelines—a commentary and an alternative European approach according to clinical definitions." Eur J Med Res. Mar. 28, 2011;16(3):115-26.
Hasper, et al., "Management of severe abdominal infections." Recent Pat Antiinfect Drug Discov. Jan. 2009;4(1):57-65.
Krobot, et al., "Effect of inappropriate initial empiric antibiotic therapy on outcome of patients with community-acquired intra-abdominal infections requiring surgery." Eur J Clin Microbiol Infect Dis. Sep. 2004;23(9):682-7.
Rotun, et al., "*Staphylococcus aureus* with reduced susceptibility to vancomycin isolated from a patient with fatal bacteremia." Emerg Infect Dis. Jan.-Feb. 1999;5(1):147-9.

(Continued)

*Primary Examiner* — Elly-Gerald Stoica
(74) *Attorney, Agent, or Firm* — Knobbe, Martens, Olson & Bear, LLP

(57) ABSTRACT

The present invention provides compositions comprising granulocyte-macrophage colony-stimulating factor and anti-microbial agents for the treatment, pre-emptive treatment or prevention of infectious peritonitis or intra-abdominal infection by intraperitoneal administration of the compositions.

17 Claims, No Drawings
Specification includes a Sequence Listing.

(56) References Cited

OTHER PUBLICATIONS

Solomkin et al., Guidelines for the selection of anti-infective agents for complicated intra-abdominal infections., Clin. Infect. Dis. 37, 997-1005, 2003.

Bandera et al., Interferon-y and granulocyte-macrophage colony stimulating factor therapy in three patients with pulmonary Aspergillosis. Infection, 36, 368-373, 2008.

Palgi et al., Delivery of cytokines by liposomes. III. Liposomeencapsulated GM-CSF and TNF-alpha show improved pharmacokinetics and biological activity and reduced toxicity in mice. J. Immunother. 20, 180-193, 1997.

Berglund et al. The dynamics of intraperitoneal growth and elimination of *Escherichia coli* and Bacteroides fragilis in porcine faecal peritonitis treated with fosfomycin, J. Antimicrob. Chemother. 27, 527-533, 1991.

Kawaguchi et al., Time- and dose-dependent effect of fosfomycin on suppression of infection-induced endotoxin shock in mice, Biol. Pharm. Bull. 25, 1658-1661, 2002.

Falagas et al. Fosfomycin: Use beyond urinary tract and gastrointestinal infections. Clin. Infect. Dis. 46, 1069-1077, 2008.

E.J.C. Goldstein: "Intra-abdominal infections: review of the bacteriology, antimicrobial susceptibility and the rose of ertapenem in their therapy", Journal of Antimicrobial Chemotherapy, vol. 53, No. sup_2, May 1, 2004 (Mar. 1, 2004) pp. ii29-ii36.

Communication pursuant to Article 94(3) EPC dated Mar. 28, 2019 in EP 15 747 491.7-112, which corresponds to the present application.

Schaumann et al. "In Vitro Activities of Clindamycin, Imipenem, Metronidazole, and Piperacillin-Tazobactam against Susceptible and Resistant Isolates of Bacteroides fragilis Evaluated by Kill Kinetics"; Antimicrobial Agents and Chemotherapy, Jun. 2012, vol. 56, No. 6, p. 3413-3416.

Kam-Tao Li et al: International Peritoneal Dialysis Society Guidelines/ Recommendations, Current Topics on Peritoneal Dialysis, 2010, vol. 27, Supplement 1, p. 1-38, [Access date: May 17, 2019], URL, http://www.baxter.co.jp/therapies/kidney/ctpd/2701.pdf) [No English version available].

Rawat et al: The Pharmaceutical Society of Japan, 2008, vol. 128, No. 2, p. 269-280.

Notice of Reasons for Rejection dated Jun. 3, 2019 in Japanese Application No. 2017-506864, which corresponds to the present application (English translation provided).

* cited by examiner

SEQUENCE LISTING

```
<160> NUMBER OF SEQ ID NOS: 2

<210> SEQ ID NO 1
<211> LENGTH: 144
<212> TYPE: PRT
<213> ORGANISM: Homo Sapiens

<400> SEQUENCE: 1

Met Trp Leu Gln Ser Leu Leu Leu Gly Thr Val Ala Cys Ser Ile
1               5                   10                  15

Ser Ala Pro Ala Arg Ser Pro Ser Pro Ser Thr Gln Pro Trp Glu His
                20                  25                  30

Val Asn Ala Ile Gln Glu Ala Arg Arg Leu Leu Asn Leu Ser Arg Asp
            35                  40                  45

Thr Ala Ala Glu Met Asn Glu Thr Val Glu Val Ile Ser Glu Met Phe
        50                  55                  60

Asp Leu Gln Glu Pro Thr Cys Leu Gln Thr Arg Leu Glu Leu Tyr Lys
65                  70                  75                  80

Gln Gly Leu Arg Gly Ser Leu Thr Lys Leu Lys Gly Pro Leu Thr Met
                85                  90                  95

Met Ala Ser His Tyr Lys Gln His Cys Pro Pro Thr Pro Glu Thr Ser
                100                 105                 110

Cys Ala Thr Gln Ile Ile Thr Phe Glu Ser Phe Lys Glu Asn Leu Lys
            115                 120                 125

Asp Phe Leu Leu Val Ile Pro Phe Asp Cys Trp Glu Pro Val Gln Glu
        130                 135                 140

<210> SEQ ID NO 2
<211> LENGTH: 127
<212> TYPE: PRT
<213> ORGANISM: Homo Sapiens

<400> SEQUENCE: 2

Ala Pro Ala Arg Ser Pro Ser Pro Ser Thr Gln Pro Trp Glu His
1               5                   10                  15
```

-continued

| | | | | | | | | | | | | | |
|---|---|---|---|---|---|---|---|---|---|---|---|---|---|
| Val | Asn | Ala | Ile | Gln | Glu | Ala | Arg | Arg | Leu | Leu | Asn | Leu | Ser | Arg | Asp |
| | | | | 20 | | | | | 25 | | | | | 30 | |
| Thr | Ala | Ala | Glu | Met | Asn | Glu | Thr | Val | Glu | Val | Ile | Ser | Glu | Met | Phe |
| | | | 35 | | | | | 40 | | | | | 45 | | |
| Asp | Leu | Gln | Glu | Pro | Thr | Cys | Leu | Gln | Thr | Arg | Leu | Glu | Leu | Tyr | Lys |
| | | 50 | | | | | 55 | | | | | 60 | | | |
| Gln | Gly | Leu | Arg | Gly | Ser | Leu | Thr | Lys | Leu | Lys | Gly | Pro | Leu | Thr | Met |
| | 65 | | | | | 70 | | | | | 75 | | | | |
| Met | Ala | Ser | His | Tyr | Lys | Gln | His | Cys | Pro | Pro | Thr | Pro | Glu | Thr | Ser |
| 80 | | | | | 85 | | | | | 90 | | | | | 95 |
| Cys | Ala | Thr | Gln | Ile | Ile | Thr | Phe | Glu | Ser | Phe | Lys | Glu | Asn | Leu | Lys |
| | | | | 100 | | | | | 105 | | | | | 110 | |
| Asp | Phe | Leu | Leu | Val | Ile | Pro | Phe | Asp | Cys | Trp | Glu | Pro | Val | Gln | Glu |
| | | | 115 | | | | | 120 | | | | | 125 | | |

METHODS FOR INHIBITING INFECTIOUS PERITONITIS

CROSS-REFERENCE TO RELATED APPLICATIONS

The present application is a divisional application of U.S. patent application Ser. No. 15/502,118 filed on Feb. 6, 2017, which is a national phase application of International Patent Application No. PCT/EP2015/068269, filed Aug. 7, 2015, which claims priority to Denmark Application No. PA201470473, filed Aug. 7, 2014. The entire contents of these applications are hereby expressly incorporated by reference in their entireties.

Any and all applications for which a foreign or domestic priority claim is identified in the Application Data Sheet as filed with the present application are hereby incorporated by reference under 37 CFR 1.57.

REFERENCE TO SEQUENCE LISTING

A Sequence Listing submitted as an ASCII text file via EFS-Web is hereby incorporated by reference in accordance with 35 U.S.C. § 1.52(e). The name of the ASCII text file for the Sequence Listing is SeqList-ZACCO178-007d1.txt, the date of creation of the ASCII text file is Oct. 18, 2018, and the size of the ASCII text file is 3 KB.

FIELD OF INVENTION

The present invention provides compositions comprising granulocyte-macrophage colony-stimulating factor (GM-CSF) in combination with one or more antimicrobial agents for the prophylaxis, pre-emptive treatment or treatment of peritonitis of microbial causation by direct instillation into the peritoneal cavity. As such, it will be useful in the fields of abdominal surgery, gastroenterology and even nephrology, for patients receiving peritoneal dialysis.

BACKGROUND OF INVENTION

Peritonitis is defined as inflammation of the peritoneum, the serosal membrane that lines the abdominal cavity and covers the organs within it. The peritoneum, which is normally sterile, reacts to various pathologic stimuli with a fairly uniform inflammatory response. Depending on the underlying pathology, the resulting peritonitis may be infectious or sterile in origin (Daley 2013).

Sterile or aseptic peritonitis may be caused by irritants such as foreign bodies, bile from a perforated gall bladder or a lacerated liver, gastric acid from a perforated ulcer or fluid from a ruptured ovarian cyst, or may result from genetically determined disorders such as polyserositis or familial Mediterranean fever and autoimmune diseases such as systemic lupus erythematosus.

Infectious peritonitis is caused by the entry of microorganisms into the abdominal cavity. It is conventionally classified into primary, secondary or tertiary peritonitis (see Holzheimer 2001).

Primary infectious peritonitis refers to spontaneous microbial invasion of the peritoneal cavity. It is often called spontaneous bacterial peritonitis. This mainly occurs in infancy and early childhood, in cirrhotic patients with ascites and immunocompromised patients.

Secondary infectious peritonitis, usually bacterial, refers to peritoneal infections secondary to intra-abdominal lesions, such as perforation of the hollow viscus, bowel necrosis, penetrating infectious processes or bacterial infection consequential to an originally aseptic peritonitis.

Peritoneal dialysis-associated peritonitis is a regrettably common, special type of secondary infectious peritonitis resulting from bacterial contamination introduced by peritoneal dialysis, an increasingly widespread treatment for end-stage renal failure.

Tertiary peritonitis is a less well-defined entity characterized by persistent or recurrent infections with organisms of low intrinsic virulence or with predisposition for the immunocompromised patient. It usually follows operative attempts to treat secondary peritonitis and is almost exclusively associated with a systemic inflammatory response.

Infectious peritonitis is often used synonymously with intra-abdominal infection or sepsis. In assessing the significance of the presence of microorganisms in the peritoneal cavity, it may be useful to distinguish between contamination (the presence of bacteria in normal sterile tissue without any host reaction), infection (the presence of bacteria in normal sterile tissue with a local inflammatory response), and sepsis (the systemic response to local infection).

A small proportion of cases of infectious peritonitis (1-5%) are caused by fungi, most commonly by *Candida albicans*, but also by other fungi in rare instances.

Clinically, peritonitis is often classified as either as local or diffuse. Local peritonitis refers to a site of infection, usually walled-off or contained by adjacent organs, and may also be called an intra-abdominal abscess. Diffuse peritonitis is synonymous with generalized peritonitis that spreads to the entire abdominal cavity.

The incidence of aseptic peritonitis, with its disparate causes, has not been globally assessed. The incidence of non-sporadic causes relates to the prevalence of familial Mediterranean fever and to a fraction of patients with systemic lupus erythematosus. Global figures are also lacking for primary infectious peritonitis, but this has been estimated to affect 10-30% of all patients admitted to hospital with ascites (Wiest et al 2012). The incidence of secondary peritonitis is similarly difficult to assess. Intra-abdominal infections occur in 25% of patients with multiple organ failure in surgical ICU. Peritonitis was present in 8% of all cases in a large necropsy series. Peritoneal dialysis-associated peritonitis occurs in 50-60% of patients within the first year of dialysis and recurrent episodes are common. Overall, it can be estimated that cases of secondary peritonitis, constituting by far the largest proportion of all peritonitis cases, must amount to several hundred thousand patients per year in the USA and Europe.

Granulocyte-Macrophage Colony-Stimulating Factor (GM-CSF) in Peritonitis

GM-CSF is a cytokine of the colony-stimulating factor family which is secreted by macrophages, T cells, mast cells, natural killer (NK) cells, endothelial cells and fibroblasts. It is also secreted by the peritoneal mesothelial cells, the main fixed cell component of the peritoneal membrane. Secretion from these cells may be spontaneous in culture or upregulated by Interleukin (IL)-1 (Lanfrancone et al 1992), or induced by epidermal growth factor (EGF) and tumor necrosis factor (TNF) (Demetri et al 1989). GM-CSF functions as a white blood cell growth factor, stimulating stem cells to produce granulocytes (neutrophils, eosinophils, and basophils) and monocytes. Monocytes exit the circulation and migrate into tissue, whereupon they mature into macrophages and dendritic cells. GM-CSF stimulates the proliferation and maturation of macrophages into dendritic cells, which orchestrate the responses of the surrounding neutrophils and T lymphocytes to local infectious/inflammatory processes.

In severe infections such as bacterial peritonitis, the normal immuno-inflammatory defense mechanisms involving macrophages, neutrophils and lymphocytes may not always function optimally for the patient's recovery. Volk et al (1991) described the loss of HLA-class II antigen expression and other phenotypical abnormalities of monocytes from patients with septic peritonitis and fatal outcome. These abnormalities were associated with functional defects of antigen presentation, formation of reactive oxygen species and cytokine secretion. This phenomenon was termed "immunoparalysis", and its leading feature, the loss of HLA-DR antigen expression to <20%, was reversed by GM-CSF and interferon-gamma in vitro.

However, attempting to restore monocyte/macrophage function in bacterial peritonitis by giving systemic GM-CSF has given rise to contradictory results. Toda et al (1994) treated rats with peritonitis induced by cecal ligation and puncture with recombinant murine GM-CSF. The survival rate did not improve and animals died earlier than in the control group. Systemic GM-CSF inhibited early leukocyte sequestration in the peritoneal cavity. It was concluded that "care should be taken" in the clinical use of GM-CSF in severe infection. Similarly, Barsig et al (1996) found that prophylactic administration (by an unstated route) of murine GM-CSF neither augmented leukocyte numbers nor protected mice in a sub-lethal model of fecal peritonitis.

In contrast, Gennari et al (1994) found that subcutaneous injection of GM-CSF significantly reduced the mortality of mice that had been immunosuppressed by allogenic transfusion and subjected to cecal ligation and puncture. Macrophage and leukocyte numbers and function were not recorded. Austin et al (1995) demonstrated a prophylactic effect of intraperitoneal GM-CSF given to mice for 5 days after a traumatic injury and before inducing bacterial peritonitis by cecal ligation and puncture. This procedure improved survival, increased the yield of harvested peritoneal cells, improved aspects of peritoneal macrophage function and reduced bacterial growth indices.

In human patients with non-traumatic generalized abdominal sepsis treated with systemic antibiotics, subcutaneously administered GM-CSF reduced the rate of infectious complications and length of hospitalization (Orozco et al 2006).

Selgas et al (1996) tested the effects of intraperitoneally administered GM-CSF on the number and activation of peritoneal macrophages in peritoneal dialysis patients. There was a large increase in peritoneal macrophage numbers returning to baseline seven days after cessation of treatment. GM-CSF increased macrophage expression of CD11b/CD18 (CR3) and its counter-receptor CD54, indicating progression to a more activated state. Both the number of phagocytic cells and the phagocytic index were augmented. Peritoneal effluent cytokine-chemokine levels demonstrated an increase in IL-6 and MCP-1 levels, while TNF-alpha, IL-1, IL-8, MIP-1 alpha and RANTES were not significantly altered. GM-CSF administration did not affect the peritoneal transport of water or solutes. Minor flu-like symptoms were experienced by 2 of 8 patients (those showing the highest rise in cell numbers) on the third and last day of treatment. It was concluded that GM-CSF causes a marked and transient recruitment of primed macrophages into the peritoneum without inducing inflammatory parameters and might thus improve the peritoneal defensive capacity through potentiation of the effector functions of resident and newly recruited macrophages.

In a follow-up study, Schafer et al (1998) determined that the peritoneal macrophages were the likely source of the chemokines released upon intraperitoneal administration of GM-CSF.

Antimicrobial Treatment of Bacterial Peritonitis

Treatment of infectious peritonitis involves correction of the underlying process, such as leakage of bacteria from a bowel perforation, administration of systemic antibiotics, and supportive therapy to prevent or limit secondary complications due to organ failure (Daley 2013). Early control of the septic source is mandatory and can be achieved operatively or non-operatively.

Antimicrobial/antibiotic treatment is regarded as essential and may be applied before, during and after any surgical procedure to correct the underlying cause of infection. Antibiotic regimens with little or no activity against Gram-negative rods or anaerobic Gram-negative rods are not considered acceptable (Holzheimer 2001).

Organisms found in acute infectious peritonitis include *Escherichia coli*, followed by the anaerobic *Bacteroides fragilis* group, Gram-positive anaerobic cocci, *Enterococcus* spp. and *Klebsiella* spp. (Shinagawa et al 1994). In postoperative peritonitis, the order of frequency of organisms was found to be *Enterococcus* spp. followed by *Pseudomonas* spp., *Staphylococcus* spp., *E. coli*, *Enterobacter* spp. and *Klebsiella* spp. (8%). In a study of 100 cases of infectious peritonitis in India, Shree et al (2013) found *E. coli* to be the predominant aerobic pathogen, followed by *Klebsiella* spp., while *Bacteroides fragilis* was the predominant anaerobe. Fungi were only recovered in 3 cases. Approximately two-thirds of *E. coli* and *Klebsiella* spp. were extended range beta-lactamase (ESBL) positive and a high level of resistance was observed for beta lactams, ciprofloxacin, amikacin, and ertapenem. In a study of 58 patients with infectious peritonitis in Mexico, Orozco et al (2006) found the following microorganisms in descending order of frequency: *E. coli*, *Enterococcus* spp., *Streptococcus* spp., *Klebsiella* spp., *Pseudomonas* spp., *Enterobacter* spp., *Staphylococcus* spp., *Clostridium* spp., *Bacteroides* spp. (only 1 patient) and *Candida* spp. (2 patients). In peritonitis associated with peritoneal dialysis, infectious organisms reflect skin and environmental contamination of the dialysis catheter and fluid, and *Staphylococcus* spp. (chiefly coagulase-negative) are the most common organisms found (Troidle et al 2006).

The antibiotics recommended to treat bacterial peritonitis vary with time and place, according to the local spectrum of infections and the prevalence of antibiotic-resistant organisms, as well as the development of succeeding generations of antibiotics intended to overcome resistance. Normally a broad-spectrum bactericidal antibiotic with activity against the majority of aerobic organisms is given intravenously, together with an antibiotic active against the principal anaerobic pathogens of the *B. fragilis* group. Although the intraperitoneal route of giving antibiotics may be the most effective for treating generalized infectious peritonitis of whatever cause, this has not usually been done except in the treatment of peritonitis associated with peritoneal dialysis, where there is already an intraperitoneal catheter in place.

SUMMARY OF THE INVENTION

The purpose of the present invention is to provide the means for the optimal treatment of infectious peritonitis by both restoring defective peritoneal macrophage function by providing GM-CSF via the effective intraperitoneal route, and providing the most appropriate antibiotics to eliminate the causative organisms in this context, the antibiotics also being given by that route. The prime candidate antibiotic that is active against all the causative aerobic bacteria found in infectious peritonitis is fosfomycin. Fosfomycin is highly active against the aerobic genera *Staphylococcus, Streptococcus, Neisseria, Escherichia, Proteus, Serratia, Salmonella, Shigella, Pseudomonas, Haemophilus* and *Vibrio*, and active against *Klebsiella* and *Enterobacter* spp. (see for example, Rodriguez et al 1977). With respect to anaerobic genera, it is active against *Peptostreptococcus* (including *Peptoniphilus, Finegoldia* and *Anaerococcus*) and *Fusobacterium*, but not against bacteria of the *B. fragilis* group. Fosfomycin is highly effective against Enterobacteriaceae, including multidrug-resistant *E. coli* and ESLB-producing organisms.

Intraperitoneal administration of the antibiotic results in high local concentrations that are many times higher than the minimum inhibitory concentrations for even the organisms that are regarded as relatively resistant to fosfomycin. An advantage of fosfomycin is that it is not only remarkably non-toxic in terms of systemic adverse effects, but also that it lacks toxic effects on granulocytes, macrophages and dendritic cells, so that the effects of GM-CSF on these cells are unimpaired.

However, bacteria of the *B. fragilis* group are resistant to fosfomycin, so that in treating bacterial peritonitis in which bacteria of this group are reasonably expected to play a pathogenic role, one or more further antibiotics or antimicrobial agents with activity against this group must be provided to be given concomitantly by the same route. Non-limiting examples of such agents are metronidazole or carbapenems such as imipenem or meropenem.

In treating fungal peritonitis with intraperitoneal GM-CSF and one or more intraperitoneal antimicrobial agents, fosfomycin has no part to play and is substituted by antifungal agents, non-limiting examples of which are fluconazole or caspofungin.

The invention therefore consists of providing a means of optimizing the treatment of infectious peritonitis or intra-abdominal infection by providing GM-CSF administered intraperitoneally to improve peritoneal antimicrobial defense by restoring defective peritoneal macrophage function and recruiting further primed macrophages into the peritoneum without inducing systemic inflammation, while at the same time providing appropriate antimicrobial agents administered intraperitoneally to achieve high local bactericidal or fungicidal concentrations. Accordingly, the present invention provides the following pharmaceutical compositions for intraperitoneal administration:

1. A composition comprising granulocyte-macrophage colony-stimulating factor (GM-CSF) or a functional homologue, variant or fragment thereof together with one or more antimicrobial or antibiotic agents for the treatment, pre-emptive treatment or prophylaxis of infectious peritonitis or intra-abdominal infection, wherein the composition is for intraperitoneal administration.
2. A composition according to 1. above, wherein the antimicrobial or antibiotic agent comprises fosfomycin.
3. A composition according to 2. above, wherein the antimicrobial or antibiotic agents comprise fosfomycin and one or more additional agents that are active against bacteria of the *Bacteroides fragilis* group.
4. A composition according to 3. above, wherein the additional antimicrobial or antibiotic agent that is active against bacteria of the *Bacteroides fragilis* group is metronidazole.
5. A composition according to 3. above, wherein the additional antimicrobial or antibiotic agent that is active against bacteria of the *Bacteroides fragilis* group is imipenem.
6. A composition according to 1. above, wherein the antimicrobial or antibiotic agents comprise one or more antifungal agents, such as fluconazole or caspofungin.

A second aspect of the present invention provides a kit-of-parts for use in the treatment, pre-emptive treatment or prophylaxis of infectious peritonitis or intra-abdominal infection in a subject, where said kit comprises
  (i) a first composition comprising granulocyte-macrophage colony-stimulating factor (GM-CSF) or a functional homologue, variant or fragment thereof; and
  (ii) a second composition comprising one or more antimicrobial or antibiotic agents,
wherein said first and second compositions are for intraperitoneal administration.

A third aspect of the present invention concerns a method for the treatment, pre-emptive treatment or prophylaxis of infectious peritonitis or intra-abdominal infection in a subject, said method comprising the step of:
  (i) administering a therapeutically effective amount of a first composition comprising granulocyte-macrophage colony-stimulating factor (GM-CSF) or a functional homologue, variant or fragment thereof; and
  (ii) administering a therapeutically effective amount of a second composition comprising one or more antimicrobial or antibiotic agents,
wherein said administering is by intraperitoneal administration.

The compositions may be administered simultaneously, concurrently, separately or sequentially. The granulocyte-macrophage colony-stimulating factor (GM-CSF) or a functional homologue, variant or fragment thereof and the one or more antimicrobial or antibiotic agents may also be co-formulated in a single formulation and administrated as such.

A further aspect of the present invention concerns a pharmaceutical composition comprising granulocyte-macrophage colony-stimulating factor (GM-CSF) or a functional homologue, variant or fragment thereof together with one or more antimicrobial or antibiotic agents. In a preferred embodiment, the antimicrobial or antibiotic agents comprise fosfomycin.

In the following detailed description of the invention, details of the scope of the invention and the meaning of certain terms used will be given, together with details of the practical performance of the invention.

DETAILED DESCRIPTION OF THE INVENTION

The present invention relates to compositions for the treatment of infectious peritonitis or intra-abdominal infection. The essential features of the invention are 1) that the compositions are for local administration into the peritoneal cavity by any appropriate means, but typically at operation or via a catheter such as a Tenckhoff catheter implanted in the abdominal wall to terminate intraperitoneally; and 2) that the compositions provide GM-CSF to improve peritoneal antimicrobial defense by restoring defective peritoneal macrophage function and recruiting further primed macrophages into the peritoneum without inducing systemic inflammation, while at the same time providing appropriate antimicrobial agents to achieve high local bactericidal or fungicidal concentrations.

The GM-CSF and the antimicrobial/antibiotic agent(s) may be formulated in one composition for intraperitoneal administration. Preferably, the GM-CSF and the antimicrobial/antibiotic agent(s) are formulated in separate formulation for simultaneous, concurrent, separate or sequential administration to the peritoneal cavity.

Accordingly, a first aspect of the present invention provides a pharmaceutical composition comprising granulocyte-macrophage colony-stimulating factor (GM-CSF) or a functional homologue, variant or fragment thereof together with one or more antimicrobial or antibiotic agents for use in the treatment, pre-emptive treatment or prophylaxis of infectious peritonitis or intra-abdominal infection in a subject, wherein the composition is for intraperitoneal administration.

A second aspect of the present invention provides a kit-of-parts for use in the treatment, pre-emptive treatment or prophylaxis of infectious peritonitis or intra-abdominal infection in a subject, where said kit comprises
(i) a first composition comprising granulocyte-macrophage colony-stimulating factor (GM-CSF) or a functional homologue, variant or fragment thereof; and
(ii) a second composition comprising one or more antimicrobial or antibiotic agents,
wherein said first and second compositions are for intraperitoneal administration.

A further aspect of the present invention concerns a pharmaceutical composition comprising granulocyte-macrophage colony-stimulating factor (GM-CSF) or a functional homologue, variant or fragment thereof together with one or more antimicrobial or antibiotic agents. The composition is preferably formulated for intraperitoneal administration.

The further embodiments described herein applies to both the aspect where the GM-CSF and the antimicrobial/antibiotic agent(s) are formulated as separate formulations and where the GM-CSF and the antimicrobial/antibiotic agent(s) are formulated as a single formulation.

The use of the invention is not intended to and does not substitute the necessary surgical procedures required to repair and control the underlying cause of the infection, such as the leakage of bacteria from a bowel perforation, but is fully compatible with such procedures and can be applied both before, during and after such procedures.

The theoretical background for treatment is, as outlined above, that GM-CSF administered directly into the peritoneal cavity will restore the defective function of the peritoneal macrophages resulting from severe infection and will recruit further primed macrophages without giving rise to the general pro-inflammatory response of systemically administered GM-CSF. GM-CSF is a protein that is not expected to penetrate through the peritoneum to enter the blood stream, where its general systemic pro-inflammatory myelogenic effect would be potentially deleterious to the patient undergoing treatment for peritonitis.

Simultaneously, concurrently, separately or sequentially, one or more appropriate antimicrobial agents are administered by the same, intraperitoneal route unless the antimicrobial/antibiotic agent(s) is co-formulated with the GM-CSF and administered as such. This enables considerably higher local concentrations of the agents to be achieved than those obtained after systemic administration. The preferred agent against the aerobic bacteria typically found in infectious peritonitis is fosfomycin, which active against all of these at the intraperitoneal concentrations obtained by intraperitoneal administration. It has the special advantage of being especially active against Enterobacteriaceae, including multidrug-resistant $E.\ coli$ and ESBL-producing organisms, which are found in a high proportion of cases of infectious peritonitis (see e.g. Shree et al 2013). Fosfomycin is a small, highly diffusible molecule, showing high tissue penetration. Even is this case, intraperitoneal administration produces superior intraperitoneal levels to those obtained by intravenous administration (Tobudic et al 2012).

The combination of intraperitoneal application of GM-CSF with intraperitoneal application of appropriate antimicrobial agents will have a potent therapeutic effect in infectious peritonitis by providing the active ingredients of the compositions of the invention to the site where they are needed, there achieving a high local concentration and high local efficacy. At the same time, the reduced entry of these substances, especially GM-CSF, into the blood stream will reduce unwanted systemic effects. The therapeutic efficacy of the intraperitoneally applied compositions thus contrasts with the needlessly limited efficacy of the same active ingredients when given systemically.

Treatment with the compositions of the invention will be described in more detail below. Typically, the treatment of infectious peritonitis with the compositions of the invention will be for 2 to 14 days after any surgical intervention or decision to treat, but longer treatment periods may be required in special circumstances. Antimicrobial treatment of infectious peritonitis has customarily been continued until the patient's fever has subsided and the white blood cell count returned to normal. If the patient's condition does not improve on the initial dosage regimen, the dosage can be increased by, for example, doubling the dose, in consideration of the expected lack of adverse effects.

Active Ingredients of the Compositions of the Invention

Compositions according to the present invention comprise essentially granulocyte-macrophage-colony stimulating factor (GM-CSF) or a functional homologue, variant or fragment thereof, and antimicrobial or antibiotic agents, the preferred agents being fosfomycin and well-known agents such as metronidazole, imipenem, fluconazole and caspofungin.

Granulocyte-Macrophage Colony-Stimulating Factor (GM-CSF)

GM-CSF is a member of the family of colony-stimulating factors (CSFs), which are glycoproteins that stimulate the proliferation and maturation of hematopoietic progenitors and enhance the functional activity of mature effector cells. In brief, at the level of the immature cells, CSFs ensure the self-renewal of the staminal pool and activate the first stage of hematopoietic differentiation. In the subsequent stage, when cell proliferation is associated with a progressive acquisition of the characteristics of the mature cells, they enormously enhance the number of differentiating cells. In the terminal stage, they stimulate the circulation and the activation of mature cells.

Mature GM-CSF is a monomeric protein of 127 amino-acid residues with several potential glycosylation sites. The variable degree of glycosylation results in a molecular weight range between 14 kDa and 35 kDa. Non-glycosylated and glycosylated GM-CSF show similar activity in vitro (Cebon et al 1990). The crystallographic analysis of GM-CSF revealed a barrel-shaped structure composed of four short alpha helices (Diederichs et al 1991). There are two known sequence variants of GM-CSF. The active form of the GM-CSF protein is found extracellularly as a homodimer in vivo.

GM-CSF exerts its biological activity by binding to its receptor. The most important sites of GM-CSF receptor (GM-CSF-R) expression are on the cell surface of myeloid cells, such as macrophages types I and II, epithelial cells and endothelial cells, whereas lymphocytes are GM-CSF-R negative. The native receptor is composed of alpha and beta subunits. The alpha subunit imparts ligand specificity and binds GM-CSF with nanomolar affinity. The beta subunit is also part of the interleukin-3 and interleukin-5 receptor complexes and, in association with the GM-CSF-R alpha subunit and GM-CSF, leads to the formation of a complex with picomolar binding affinity (Hayashida et al 1990). The binding domains on GM-CSF for the receptor have been mapped: GM-CSF interacts with the beta subunit of its receptor via a very restricted region in the first alpha helix of GM-CSF (Shanafelt et al 1991a;b; Lopez et al 1991). Binding to the alpha subunit could be mapped to the third alpha helix, helix C, the initial residues of the loop joining helices C and D, and to the carboxyterminal tail of GM-CSF (Brown et al 1994).

Formation of the GM-CSF trimeric receptor complex leads to the activation of complex signaling cascades involving molecules of the JAK/STAT families, She, Ras, Raf, the MAP kinases, phosphatidylinositol-3-kinase and NFkB, finally leading to the transcription of c-myc, c-fos and c-jun. Activation is mainly induced by the beta subunit of the receptor (Hayashida et al 1990; Kitamura et al 1991; Sato et al 1993). The shared beta subunit is also responsible for the overlapping functions exerted by IL-3, IL-5 and GM-CSF (reviewed by de Groot et al 1998).

In addition to its stimulating activity on hemopoietic growth and differentiation, GM-CSF acts as a pro-inflammatory cytokine. Macrophages, e.g. macrophages type I & II and monocytes, as well as neutrophils and eosinophils, are activated by GM-CSF, resulting in the release of other cytokines and chemokines and matrix-degrading proteases, as well as increased expression of HLA and cell adhesion molecules or receptors for CC-chemokines. This in turn leads to increased chemotaxis of inflammatory cells into inflamed tissue.

For practical purposes, the GM-CSF preparations to be used in the present invention will not be purified native human GM-CSF, which could of course be used if it were available in sufficient quantity and problems of possible viral contamination were overcome, but human GM-CSF prepared in vitro by recombinant DNA technology. The preparation of human recombinant GM-CSF (hrGM-CSF) in mammalian cells has been described (Wong et al 1985; Kaushansky et al 1986). Similar work has led to the production of hrGM-CSF with the non-proprietary name regramostim in Chinese hamster ovarian (CHO) cells (first reported by Moonen et al 1987). The expression of hrGM-CSF in *Saccharomyces cerevisiae* was reported by Cantrell et al (1985), leading to the preparation known by the non-proprietary name sargramostim. Sargramostim differs from endogenous human GM-CSF in having a leucine residue instead of a proline residue at position 23 of the pro-peptide and is less glycosylated than either endogenous human GM-CSF or regramostim (Armitage 1998). The expression of hrGM-CSF in *Escherichia coli* was reported by Burgess et al (1987), leading to the preparation known by the non-proprietary name molgramostim, which is not glycosylated. All three hrGM-CSF preparations, regramostim, sargramostim and molgramostim can be used in the present invention, but only the last two are currently available.

A "functional homologue" of human GM-CSF is herein defined as a polypeptide having at least 50% sequence identity with the known and naturally occurring sequence and sequence variants of human GM-CSF and has one or more functions of the naturally occurring protein. These functions include the following: stimulating the growth and differentiation of hematopoietic precursor cells from various lineages, including granulocytes, macrophages and monocytes, enhancing functional activities of mature effector cells involved in antigen presentation and cell-mediated immunity, including neutrophils, monocytes, macrophages, and dendritic cells. The functions also include causing the local recruitment of inflammatory cells, improving the recruitment of neutrophils, activating mononuclear phagocytes, promoting the migration of epithelial cells, and further regulating cytokine production in the healing process. Regramostim, sargramostim and molgramostim may all be said to be functional homologues of naturally occurring human GM-CSF.

Evolutionary conservation between GM-CSF homologues of different closely related species, as assessed by amino-acid sequence alignment, can be used to pinpoint the degree of evolutionary pressure on individual amino-acid residues. Preferably, GM-CSF sequences are compared between species where GM-CSF function is conserved, for example, but not limited to mammals, including rodents, monkeys and apes. Residues under high selective pressure are more likely to represent essential amino acid residues that cannot easily be substituted than residues that change between species. It is evident from the above that a reasonable number of modifications or alterations of the human GM-CSF sequence can be made without interfering with the activity of the GM-CSF molecule according to the invention. Such GM-CSF molecules are herein referred to as functional homologues of human GM-CSF, and may be such variants and fragments of native human GM-CSF as described below.

As used herein, the term "variant" refers to a polypeptide or protein which is homologous to the index protein (also referred to as the parent), which is naturally occurring human GM-CSF in the present instance, but which differs from the index protein in that one or more amino-acid residues within the sequence of the index protein are substituted by other amino-acid residues. These substitutions may be regarded as "conservative" when an amino-acid residue is replaced by a different amino-acid residue with broadly similar properties, and "non-conservative" when an amino-acid residue is replaced by one of a different type. Broadly speaking, fewer non-conservative substitutions will be possible without altering the biological activity of the polypeptide. Thus, in one embodiment of the present invention GM-CSF is a variant of the human GM-CSF having the amino acid sequence set forth in SEQ ID NO: 2. In such case, the amino acid sequence set forth in SEQ ID NO: 2 is the index sequence (also referred to as the parent) from which the variants are obtained by one or more amino acid substitutions (or insertions or deletions).

A person skilled in the art will know how to make and assess "conservative" amino-acid substitutions, by which one amino-acid residue is substituted by another having one or more shared chemical and/or physical characteristics. Conservative amino-acid substitutions are less likely to affect the functionality of the protein. Amino acids may be grouped according to their shared characteristics. A conservative amino-acid substitution is a substitution of one amino acid within a predetermined group of amino acids for another amino acid within the same group, within which the amino acids exhibit similar or substantially similar characteristics. Within the meaning of the term "conservative amino acid substitution" as applied herein, one amino acid may be substituted by another within groups of amino acids characterized by having i) polar side chains (Asp, Glu, Lys, Arg, His, Asn, Gln, Ser, Thr, Tyr and Cys)
ii) non-polar side chains (Gly, Ala, Val, Leu, Ile, Phe, Trp, Pro and Met)
iii) aliphatic side chains (Gly, Ala Val, Leu and Ile)
iv) cyclic side chains (Phe, Tyr, Trp, His and Pro)
v) aromatic side chains (Phe, Tyr and Trp)
vi) acidic side chains (Asp and Glu)
vii) basic side chains (Lys, Arg and His)
viii) amide side chains (Asn and Gln)
ix) hydroxyl side chains (Ser and Thr)
x) sulfur-containing side chains (Cys and Met)
xi) amino acids being monoamino-dicarboxylic acids or monoamino-monocarboxylic-monoamidocarboxylic acids (Asp, Glu, Asn and Gln).

A functional homologue within the scope of the present invention is a polypeptide that exhibits at least 50% sequence identity with a naturally occurring form of human GM-CSF, such as at least 60% sequence identity, for example at least 70% sequence identity, such as at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with a naturally occurring form of human GM-CSF.

Sequence identity can be calculated using a number of well-known algorithms and applying a number of different gap penalties. Any sequence alignment algorithm, such as but not limited to FASTA, BLAST, or GETSEQ, may be used for searching homologues and calculating sequence identity. Moreover, when appropriate, any commonly known substitution matrix, such as but not limited to PAM, BLOSSUM or PSSM matrices, may be applied with the search algorithm. For example, a PSSM (position specific scoring matrix) may be applied via the PSI-BLAST program. Moreover, sequence alignments may be performed using a range of penalties for gap-opening and extension. For example, the BLAST algorithm may be used with a gap-opening penalty in the range 5-12, and a gap-extension penalty in the range 1-2.

Accordingly, a variant or a fragment thereof according to the invention may comprise, within the same variant of the sequence or fragments thereof, or among different variants of the sequence or fragments thereof, at least one substitution, such as a plurality of substitutions introduced independently of one another.

It is clear from the above outline that the same variant or fragment thereof may comprise more than one conservative amino-acid substitution from more than one group of conservative amino acids as defined herein above.

Aside from the twenty standard amino acids and two special amino acids, selenocysteine and pyrrolysine, there are a vast number of "non-standard amino acids" which are not incorporated into protein in vivo. Examples of nonstandard amino acids include the sulfur-containing taurine, the neurotransmitter GABA and the neurotransmitter precursor L-DOPA. Other examples are lanthionine, 2-aminoisobutyric acid, and dehydroalanine. Further non-standard amino are ornithine and citrulline.

Non-standard amino acids are usually formed through modifications to standard amino acids. For example, taurine can be formed by the decarboxylation of cysteine, while dopamine is synthesized from tyrosine and hydroxyproline is made by a posttranslational modification of proline (common in collagen). Examples of non-natural amino acids are those listed e.g. in 37 C.F.R. section 1.822(b)(4), all of which are incorporated herein by reference.

Both standard and non-standard amino acid residues described herein can be in the "D" or "L" isomeric form.

It is contemplated that a functional equivalent according to the invention may comprise any amino acid including non-standard amino acids. In preferred embodiments, a functional equivalent comprises only standard amino acids.

The standard and/or non-standard amino acids may be linked by peptide bonds or by non-peptide bonds. The term peptide also embraces post-translational modifications introduced by chemical or enzyme-catalyzed reactions, as are known in the art. Such post-translational modifications can be introduced prior to partitioning, if desired. Amino acids as specified herein will preferentially be in the L-stereoisomeric form. Amino acid analogs can be employed instead of the 20 naturally occurring amino acids. Several such analogs are known, including fluorophenylalanine, norleucine, azetidine-2-carboxylic acid, S-aminoethyl cysteine, 4-methyl tryptophan and the like.

In one embodiment of the present invention, the GM-CSF variant comprises a conjugate capable of prolonging half-life of the active ingredient, such as for example albumin or a fatty acid.

Suitable variants will be at least 60% identical, preferably at least 70%, and accordingly, variants preferably have at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with the predetermined sequence of a naturally occurring form of human GM-CSF.

Functional homologues may further comprise chemical modifications such as ubiquitination, labeling (e.g., with radionuclides, various enzymes, etc.), pegylation (derivatization with polyethylene glycol), or by insertion (or substitution by chemical synthesis) of amino acids such as ornithine, which do not normally occur in human proteins.

In addition to the peptidyl compounds described herein, sterically similar compounds may be formulated to mimic the key portions of the peptide structure and such compounds may also be used in the same manner as the polypeptides of the invention. This may be achieved by techniques of modelling and chemical designing known to those of skill in the art. For example, esterification and other alkylations may be employed to modify the amino terminus (N-terminus) of, e.g., a di-arginine peptide backbone, to mimic a tetrapeptide structure. It will be understood that all such sterically similar constructs fall within the scope of the present invention.

Peptides with N-terminal alkylations and C-terminal esterifications are also encompassed by the present invention. Functional equivalents also comprise glycosylated and covalent or aggregative conjugates formed with the same molecules, including dimers or unrelated chemical moieties. Such functional equivalents are prepared by linkage of functionalities to groups which are found in a fragment that includes any one or both of the N- and C-termini, by means known in the art.

The term "fragment thereof" may refer to any portion of the given amino-acid sequence. Fragments may comprise more than one portion from within the full-length protein, joined together. Suitable fragments may be deletion or addition mutants. The addition of at least one amino acid may be an addition of from preferably 2 to 250 amino acids, such as from 10 to 20 amino acids, for example from 20 to 30 amino acids, such as from 40 to 50 amino acids. Fragments may include small regions from the protein or combinations of these. The deletion and/or the addition may independently of one another be a deletion and/or an addition within a sequence and/or at the end of a sequence.

Deletion mutants suitably comprise at least 20 or 40 consecutive amino acid and more preferably at least 80 or 100 consecutive amino acids in length. Accordingly, such a fragment may be a shorter sequence taken from the sequence of human GM-CSF comprising at least 20 consecutive amino acids, for example at least 30 consecutive amino acids, such as at least 40 consecutive amino acids, for example at least 50 consecutive amino acids, such as at least 60 consecutive amino acids, for example at least 70 consecutive amino acids, such as at least 80 consecutive amino acids, for example at least 90 consecutive amino acids, such as at least 95 consecutive amino acids, such as at least 100 consecutive amino acids, such as at least 105 amino acids, for example at least 110 consecutive amino acids, such as at least 115 consecutive amino acids, for example at least 120 consecutive amino acids, wherein said deletion mutants preferably has at least 75% sequence identity, for example at least 80% sequence identity, such as at least 85% sequence identity, for example at least 90% sequence identity, such as at least 91% sequence identity, for example at least 91% sequence identity, such as at least 92% sequence identity, for example at least 93% sequence identity, such as at least 94% sequence identity, for example at least 95% sequence identity, such as at least 96% sequence identity, for example at least 97% sequence identity, such as at least 98% sequence identity, for example 99% sequence identity with a naturally occurring form of human GM-CSF.

It is preferred that functional homologues of GM-CSF comprise at most 500, more preferably at most 400, even more preferably at most 300, yet more preferably at most 200, such as at most 175, for example at most 160, such as at most 150 amino acids, for example at most 144 amino acids.

There are two known naturally occurring variants of human GM-CSF: a T115I substitution in variant 1 and an I117T substitution in variant 2. Accordingly, in one embodiment of the invention, a functional homologue of GM-CSF comprises a sequence with high sequence identity to human GM-CSF NO: 2 or any of the naturally occurring variants.

Analogues of GM-CSF are, for example, described in U.S. Pat. Nos. 5,229,496, 5,393,870, and 5,391,485. Such analogues are also functional equivalents comprised within the present invention.

In one embodiment of the present invention, the variant, functional homologue or analogue of GM-CSF displays biological activity in a human bone marrow assay.

In one embodiment, GM-CSF is used according to the present invention in homo- or heteromeric form. Homo- and heteromeric forms of GM-CSF may comprise one or more GM-CSF monomers or functional homologous of GM-CSF as defined herein above. Homo- and heteromers include dimers, trimers, tetramers, pentamers, hexamers, heptamers, octamers, nonamers and decamers.

In one embodiment, a homodimer, trimer or tetramer of GM-CSF is used.

The amino-acid sequence of the precursor (including the signal peptide) form of GM-CSF of Homo sapiens (SEQ ID NO: 1) is:

```
MWLQSLLLLG TVACSISAPA RSPSPSTQPW EHVNAIQEAR

RLLNLSRDTA AEMNETVEVI SEMFDLQEPT CLQTRLELYK

QGLRGSLTKL KGPLTMMASH YKQHCPPTPE TSCATQIITF

ESFKENLKDF LLVIPFDCWE PVQE.
```

The amino-acid sequence of the corresponding mature protein (SEQ ID NO: 2) is:

```
APARSPSPST QPWEHVNAIQ EARRLLNLSR DTAAEMNETV

EVISEMFDLQ EPTCLQTRLE LYKQGLRGSL TKLKGPLTMM

ASHYKQHCPP TPETSCATQI ITFESFKENL KDFLLVIPFD

CWEPVQE.
```

Functional homologues of a naturally occurring form of human GM-CSF according to the present invention may be commercially available, e.g. sargramostim (Leukine®; Sanofi U S, Bridgewater, N.J., USA).

Recombinant Production of GM-CSF

GM-CSF or functional variants or homologues thereof can be produced in various ways, such as isolation from for example human or animal serum or from expression in cells, such as prokaryotic cells, yeast cells, insect cells, mammalian cells or in cell-free systems.

In one embodiment of the invention, GM-CSF is produced recombinantly by host cells. Thus, in one aspect of the present invention, GM-CSF is produced by host cells comprising a first nucleic acid sequence encoding the GM-CSF operably associated with a second nucleic acid sequence capable of directing expression in said host cells. The second nucleic acid sequence may thus comprise or even consist of a promoter that will direct the expression of protein of interest in said cells. A skilled person will be readily capable of identifying useful second nucleic acid sequence for use in a given host cell.

The process of producing a recombinant GM-CSF in general comprises the steps of
  providing a host cell
  preparing a gene expression construct comprising a first nucleic acid sequence encoding the GM-CSF operably linked to a second nucleic acid sequence capable of directing the expression of said protein of interest in the host cell
  transforming the host cell with the construct
  cultivating the host cell, thereby obtaining expression of the GM-CSF.

The recombinant GM-CSF thus produced may be isolated by any conventional method, such as any of the methods for protein isolation described herein below. The skilled person will be able to identify suitable protein isolation steps for purifying the GM-CSF.

In one embodiment of the invention, the recombinantly produced GM-CSF is excreted by the host cells. When the GM-CSF is excreted, the process of producing a recombinant protein of interest may comprise the steps of providing a host cell preparing a gene expression construct comprising a first nucleic acid sequence encoding the GM-CSF operably linked to a second nucleic acid sequence capable of directing the expression of said protein of interest in said host cell transforming said host cell with the construct cultivating the host cell, thereby obtaining expression of the GM-CSF and secretion of the GM-CSF into the culture medium thereby obtaining culture medium containing the GM-CSF.

The composition comprising GM-CSF and nucleic acids may thus in this embodiment of the invention be the culture medium or a composition prepared from the culture medium.

In another embodiment of the invention, said composition is an extract prepared from animals, parts thereof or cells or an isolated fraction of such an extract.

In an embodiment of the invention, the GM-CSF is recombinantly produced in vitro in host cells and isolated from cell lysate, cell extract or from tissue culture supernatant. In a more preferred embodiment, the GM-CSF is produced by host cells that are modified in such a way that they express the relevant GM-CSF. In an even more preferred embodiment of the invention, said host cells are transformed to produce and excrete the relevant GM-CSF.

Compositions according to the present invention may comprise GM-CSF or functional variants or homologues thereof at doses of 5 microgram to 1000 microgram, such that when added to 500 mL to 3000 mL of fluid suitable for instillation into the peritoneal cavity, concentrations of 1.67 microgram per liter to 2 milligram per liter can be obtained.

Fosfomycin

Fosfomycin is the international non-proprietary name of a broad-spectrum antibiotic isolated and characterized in 1969 from *Streptomyces fradiae* strains under the name phosphomycin or phosphonomycin (Hendlin et al 1969). Its structure was determined to be (−)(IR,2S)-1,2-epoxypropylphosphonic acid (Christensen et al 1969), with the systematic (IUPAC) name [(2R,3S)-3-methyloxiran-2-yl]phosphonic acid and a formula weight of 138.1 Da. Fosfomycin is bactericidal and inhibits bacterial cell wall biosynthesis by inactivating the enzyme UDP-N-acetylglucosamine-3-enolpyruvyltransferase, also known as MurA (Brown et al 1995). This enzyme catalyzes the committed step in peptidoglycan biosynthesis, the ligation of phosphoenolpyruvate to the 3'-hydroxyl group of UDP-N-acetylglucosamine to form N-acetylmuramic acid. Fosfomycin is a phosphoenolpyruvate analogue that inhibits MurA by alkylating an active site cysteine residue. The antibiotic enters the bacterial cell via the glycerophosphate transporter.

Given this mechanism of action, fosfomycin has a broad bactericidal spectrum, being active against aerobic genera such as *Staphylococcus, Streptococcus, Neisseria, Escherichia, Proteus* (indole-negative), *Serratia, Salmonella, Shigella, Pseudomonas, Haemophilus*, and *Vibrio*, less active against indole-positive *Proteus* spp., *Klebsiella* and *Enterobacter* spp. It is known to be active against the anaerobic genera *Peptostreptococcus* (including *Peptoniphilus, Finegoldia* and *Anaerococcus*) and *Fusobacterium*.

There is a low prevalence of bacterial resistance to fosfomycin in the community, and studies of the prevalence of resistant bacteria after the introduction of fosfomycin have shown either no increase or only a modest increase in the prevalence of resistant organisms. However, prolonged exposure to the antibiotic may enable bacteria to evolve resistance by selection of mutants that lack the glycerophosphate transporter pathway. Alternative mechanisms of resistance involve the loss of the inducible hexose phosphate transporter, a Cys-Asp mutation in MurAS, or acquistion of plasmids coding for the fosfomycin inactivating enzymes fosA and fosB (in addition to the chromosomal fosX in *Listeria monocytogenes*). The mutant strains may, however, also show reduced pathogenicity (Karageorgopoulos et al 2012). This may explain why the emergence of bacterial resistance is seen on prolonged exposure in vitro, but much less frequently in vivo. The appearance of resistant bacterial strains in controlled clinical trials of orally or intravenously administered fosfomycin has been 3.0% overall, with a maximum of 15% for *Pseudomonas aeruginosa*. In general, fosfomycin is seen to be a valuable addition to the therapeutic armament against multidrug-resistant organisms.

Fosfomycin has proved to be remarkably non-toxic to mammalian cells and organs, despite fosfomycin disodium being used at intravenous doses of up to 0.5 g/kg/day in human patients. Here the limiting factor is overload with the counter-ion rather than any toxic effect of the antibiotic. Indeed, fosfomycin has been found to exert a protective effect against the toxic action of other antibiotics, immunosuppressive or chemotherapeutic agents such as aminoglycosides, vancomycin, amphotericin B, polymyxin, cyclosporin and cisplatin (Gobernado 2003). As additional effects, it has the capacity to favor phagocytosis and act as an immunomodulator. It is accumulated by polymorphonuclear leukocytes to reach concentrations that are twice those of the extracellular fluid, but does not affect their cellular functions, while exerting a bactericidal effect on *Staphylococcus aureus*. The chief adverse effects are gastric irritation from orally administered fosfomycin disodium, evidence of allergy in the form of transient rashes (0.3% of cases) and eosinophilia (0.2%), and transiently raised liver enzymes (0.3% of cases) (Gobernado 2003).

Fosfomycin shows a considerable synergism in bactericidal effect on a large number of strains of organisms from the susceptible genera mentioned, when used in combination with a large number of antibiotics of the penicillin, cephalosporin, aminoglycoside, macrolide and lincosamide types. While early studies showed a synergistic effect on about 70-100% of tested strains for various antibiotic combinations, subsequent more extensive studies showed synergy rates of 36-74%. The remaining strains showed merely additive effects and an inhibitory effect was only seen in one or two individual antibiotic combinations on an individual bacterial strain (Gobernado 2003). However, in a specific study of an animal model of infectious peritonitis, fosfomycin showed synergy and high in-vivo efficacy with imipenem (Pachón-Ibáñez et al 2011). The fact that fosfomycin shows synergy with many individual antibiotics and indeed abrogates the toxicity of many other antibiotics, including the nephrotoxicity and ototoxicity of the aminoglycosides, favors the use of fosfomycin in combination with other antibiotics to produce a potent bactericidal action and compensate for any development of fosfomycin resistance during more prolonged treatment.

The principal forms of fosfomycin that come within the scope of this invention are:

i) Fosfomycin disodium, formula weight 182.0 Da, pH of 5% solution 9.0-10.5. This salt is highly soluble in water, but is locally irritant if un-neutralized.

ii) Fosfomycin trometamol, formula weight 259.2 Da, pH of 5% solution 3.5-5.5. This salt is highly soluble in water and is well tolerated when given orally.

When the name "fosfomycin" is used herein, it refers to an inorganic or organic salt of fosfomycin as exemplified by the principal forms above, and the dose of fosfomycin refers to the amount of the free acid form of fosfomycin present in the salt.

Compositions according to the present invention may comprise fosfomycin such that single doses give fosfomycin concentrations in the range of 1 gram to 4 gram per liter when dissolved in 500 mL to 3000 mL of fluid suitable for instillation into the peritoneal cavity. This implies doses in the range of 500 milligram to 12 gram of fosfomycin.

Other Antimicrobial Agents

Compositions according to the present invention may comprise one or more antimicrobial agents that are active against anaerobic bacteria including bacteria of the *B. fragilis* group. Any agent of this type fulfilling the criteria of being chemically compatible with fosfomycin and suitable for instillation in the peritoneal cavity when dissolved in a suitable fluid for such instillation may be used; preferred non-limiting examples comprise metronidazole and imipenem. Compositions according to the present invention may comprise one or more antimicrobial agents that are active against *Candida* spp. and other fungi and which fulfill the same criteria of compatibility; preferred non-limiting examples comprise fluconazole and caspofungin. The doses of these antimicrobial agents are adjusted so that the maximum daily dose of the agent that is given intraperitoneally in no case exceeds the maximum recommended daily dose for intravenous administration. In many cases these agents will be effective when given intraperitoneally at considerably lower doses than those recommended for intravenous administration.

Indications for Use

The indications for the use of compositions according to the present invention are suspected or confirmed, incipient or established infectious peritonitis or intra-abdominal infection, or a high imminent risk of the same, as determined by the attending surgeon or physician according to the criteria known to the skilled person.

The effect of the use of the compositions of the invention is assessed by the attending clinician in accordance with the evolution of the affected individual's clinical signs and symptoms, usually taking into account such biomarkers as body temperature and white blood-cell count.

In one embodiment of the present invention, the subject in need of being administered with a composition of the invention is a mammal in need of treatment, pre-emptive treatment or prevention of infectious peritonitis or intra-abdominal infection.

In one embodiment, the compositions of the present invention are for use in a patient who is not a peritoneal dialysis patient, or wherein the peritonitis is not caused by the presence of a peritoneal catheter.

In one embodiment, the mammal is a human. In one embodiment, the human is a child younger than 15 years of age. In one embodiment, the human is an adult 15 years of age or older.

Formulations

Pharmaceutical compositions or formulations for use in the present invention comprise GM-CSF or functional variants or homologues thereof together with one or more antimicrobial or antibiotic agents for the treatment, pre-emptive treatment or prophylaxis of infectious peritonitis or intra-abdominal infection, wherein the composition is for intraperitoneal administration. In one embodiment, the composition comprising GM-CSF further comprises fosfomycin. In a preferred embodiment, the composition comprising GM-CSF and fosfomycin further comprises metronidazole or imipenem. Such compositions or formulations may be dissolved in a pharmaceutically acceptable carrier, preferably an aqueous carrier or diluent. A variety of aqueous carriers may be used, including, but not limited to water for injection, 0.9% saline, buffered saline, physiologically compatible buffers and the like. As the intraperitoneal administration of the compositions may be performed by the techniques of peritoneal dialysis, the compositions may be supplied in dry form for dissolution in pre-prepared sterile peritoneal dialysis fluid. The compositions may be sterilized by conventional techniques well known to those skilled in the art. The resulting aqueous solutions may be packaged for use or filtered under aseptic conditions and freeze-dried, the freeze-dried preparation being dissolved in a sterile aqueous solution such as peritoneal dialysis fluid prior to administration. In one embodiment, a freeze-dried preparation comprising GM-CSF or functional variants or homologues thereof and fosfomycin with or without metronidazole or imipenem may be pre-packaged, for example in single dose units. In another embodiment, the constituents of the composition are supplied in a kit containing the individual constituents in dry form in separate vials, so that they can be dissolved and the dose of each that is added to the fluid for peritoneal instillation be adjusted prior to administration.

The compositions may contain pharmaceutically acceptable auxiliary substances or adjuvants, including, without limitation, pH-adjusting and buffering agents and/or tonicity adjusting agents, such as, for example, succinic acid, citric acid, sodium acetate, sodium bicarbonate, sodium lactate, sodium chloride, potassium chloride, calcium chloride, etc.

Formulations according to the present invention may comprise pharmaceutically acceptable carriers and excipients and the constituents may be presented as microspheres, liposomes, micelles, microcapsules, nanoparticles or the like. The GM-CSF component may, for example, be formulated in a liposome with an outer fatty layer with a core of water phase in which the GM-CSF component is dissolved. The preparation of such formulations are well known to those of skill in the art.

Protease inhibitors such as aprotinin and/or soybean trypsin inhibitor that are compatible with intraperitoneal use may be added to the compositions and formulations of the present invention to limit the breakdown of GM-CSF or functional variants or homologues thereof, to preserve effective concentrations of these substances during the period of dwell of the dissolved compositions in the peritoneal cavity.

The pH value of the compositions and formulations according to the present invention may be adjusted to a pH of between 3 and 10; such as between 4 and 9; such as between 4 and 8; such as between 5 and 8; such as between 6 and 8; preferably between 6.5 and 7.5 such as wherein said composition has a pH of about 7, such as 7.4.

In one embodiment, a freeze-dried preparation of a composition according to the present invention may be pre-packaged, for example in single dose units. In an even more preferred embodiment the single dose unit is a first composition which may be a preparation of fosfomycin for dissolving in an aqueous medium (added as double-distilled or deionized water, buffer solution or physiological electrolyte solution) and one or more other compositions comprising GM-CSF or functional variants or homologues thereof, and/or other active ingredients such as other antibiotics.

Example 2 gives a specimen formulation of a composition of the present invention suitable for treating bacterial peritonitis.

Administration

The compositions of the present invention are for intraperitoneal use and may be given by methods conventionally used in the art for instillation into the peritoneal cavity. This may be done at surgery, whether it be open or laparoscopic abdominal surgery, or it may conveniently be performed by techniques similar to those used for continuous or chronic peritoneal dialysis (CPD). There are two types of CPD therapy: continuous ambulatory peritoneal dialysis (CAPD) and continuous cycling peritoneal dialysis (CCPD). The former modality involves manual dialysis exchanges performed throughout the day (usually three to five) while the latter modality is performed continuously for approximately 8 to 10 hours at night using an automated cycling device. The method giving most flexibility will be similar to CAPD, with the difference that the patient is typically recumbent, not ambulatory, and the manual fluid exchanges are spread throughout the 24 hours of the day. Typically fluid volumes of 1500 mL to 3000 mL are used in fluid exchanges in adult patients. However, for the treatment of infectious peritonitis the purpose is not to dialyze, but to provide sufficient fluid containing the compositions of the invention to allow them to reach all parts of the peritoneal cavity. Hence smaller volumes can be used, such as 500 mL, 1000 mL, and 1500 mL.

Administration of solutions containing the compositions of the invention may, for example, comprise the steps of:

a. Inserting a catheter, such as a Tenckhoff catheter or similar device, through the abdominal wall to terminate with its outlet positioned in the peritoneal cavity at an appropriate site determined by the treating surgeon. This can conveniently be done at the time of surgical exploration to determine and treat the underlying cause of the infectious peritonitis, such as a bowel perforation, but can also be done before or after that by means of laparoscopy or even by a percutaneous technique.

b. Instilling a suitable volume of suitable fluid containing the composition to be used at the concentration determined by the attending clinician.

c. The dwell time of the fluid in the peritoneal cavity may from 4 hours to 24 hours, corresponding to 6 to 1 exchanges of fluid per day.

Dosage

By "effective amount" of the compositions of the present invention is meant a dose, which, when administered intraperitoneally to a subject in need thereof, achieves a concentration in the intraperitoneal solution which has a beneficial biological effect in the treatment, pre-emptive treatment or prophylaxis of infectious peritonitis or intra-abdominal infection.

Compositions according to the present invention may comprise GM-CSF or functional variants or homologues thereof are administered in an effective amount, which may be from 5 microgram to 1000 microgram per dose, such that when a dose is added to 500 mL to 3000 mL of fluid suitable for instillation into the peritoneal cavity, concentrations of 1.67 microgram per liter to 2 milligram per liter can be obtained.

Each dose can be administered once a day, twice a day, three times a day, four times a day, five times a day or six times a day.

Duration of dosage will typically range from 1 day to 14 days, such as in the range of 1 day to 2 days, for example 2 days to 3 days, such as in the range of 3 days to 4 days, for example 4-5 days, such as 5-6 days, for example 6-7 days, for example 7-14 days, or as long as symptoms and disease is detectable.

In embodiments where the compositions comprise fosfomycin, the composition may comprise single doses of from 500 milligram to 12 gram of fosfomycin dissolved in 500 mL to 3000 mL of fluid suitable for instillation into the peritoneal cavity to give fosfomycin concentrations in the range of 1 gram to 4 gram per liter. The maximum amount of fosfomycin given per day will not exceed 32 gram.

In embodiments where the compositions comprise other antimicrobial agents, such as metronidazole, imipenem, fluconazole or caspofungin, the doses of said antimicrobial agents are adjusted so that the maximum daily dose of the agent that is given intraperitoneally in no case exceeds the maximum recommended daily dose for intravenous administration.

EXAMPLES

The following non-limiting examples further illustrate the present invention.

Example 1: Sequences

```
SEQ ID NO: 1-Human pre-GM-CSF
>sp|P04141|CSF2_HUMAN Granulocyte-macrophage
colony-stimulating factor
OS = Homo sapiens
MWLQSLLLLGTVACSISAPARSPSPSTQPWEHVNAIQEARRLLNLSRDT

AAEMNETVEVISEMFDLQEPTCLQTRLELYKQGLRGSLTKLKGPLTMMA

SHYKQHCPPTPETSCATQIITFESFKENLKDFLLVIPFDCWEPVQE

SEQ ID NO: 2-mature human GM-CSF
>sp|P04141|18-144
APARSPSPSTQPWEHVNAIQEARRLLNLSRDTAAEMNETVEVISEMFDLQ

EPTCLQTRLELYKQGLRGSLTKLKGPLTMMASHYKQHCPPTPETSCATQI

ITFESFKENLKDFLLVIPFDCWEPVQE
```

Example 2

Composition of a formulation to provide an effective dose of GM-CSF together with fosfomycin and metronidazole when given intraperitoneally to treat bacterial peritonitis:

A dry powder containing human recombinant GM-CSF (as molgramostim) 10 microgram; fosfomycin disodium 2.64 gram (approximately equivalent to 2 gram of fosfomycin free acid), metronidazole 500 milligram, succinic acid 1-2 gram (amount to be determined to give a final pH of 7 when the mixture is dissolved). The dry solutes are packed in a capped, evacuated vial. The contents of the vial are dissolved in sterile water for injection 100 mL and added to 1 liter of a sterile physiological salt solution appropriate for intraperitoneal instillation. The physiological salt solution may contain, for example, sodium 132 mEq/L, calcium 3.5 mEq/L, magnesium 0.5 mEq/L, chloride 96 mEq/L and lactate 40 mEq/L.

REFERENCES

Armitage J O (1998) Emerging applications of recombinant human granulocyte-macrophage colony-stimulating factor. Blood 92:4491-4508.

Austin O M, Redmond H P, Watson W G, Cunney R J, Grace P A, Bouchier-Hayes D (1995) The beneficial effects of immunostimulation in posttraumatic sepsis. J Surg Res 59:446-449.

Barsig J, Bundschuh D S, Hartung T, Bauhofer A, Sauer A, Wendel A (1996) Control of fecal peritoneal infection in mice by colony-stimulating factors. J Infect Dis 174:790-799.

Brown C B, Pihl C E, Kaushansky K (1994) Mapping of human granulocyte-macrophage-colony-stimulating-factor domains interacting with the human granulocyte-macrophage-colony-stimulating-factor-receptor alpha-subunit. Eur J Biochem 225:873-880.

Brown E D, Vivas E I, Walsh C T, Kolter R (1995) MurA (MurZ), the enzyme that catalyzes the first committed step in peptidoglycan biosynthesis, is essential in *Escherichia coli*. J Bacteriol 177:4194-4197.

Burgess A W, Begley C G, Johnson G R, Lopez A F, Williamson D J, Mermod J J, Simpson R J, Schmitz A, DeLamarter J F (1987) Purification and properties of bacterially synthesized human granulocyte-macrophage colony stimulating factor. Blood 69:43-51.

Cantrell M A, Anderson D, Cerretti D P, Price V, McKereghan K, Tushinski R J, Mochizuki D Y, Larsen A, Grabstein K, Gillis S, et al (1985) Cloning, sequence, and expression of a human granulocyte/macrophage colony-stimulating factor. Proc Natl Acad Sci USA 82:6250-6254.

Cebon J, Nicola N, Ward M, Gardner I, Dempsey P, Layton J, Dührsen U, Burgess A W, Nice E, Morstyn G (1990) Granulocyte-macrophage colony stimulating factor from human lymphocytes. The effect of glycosylation on receptor binding and biological activity. J Biol Chem 265:4483-4491.

Christensen B G, Leanza W J, Beattie T R, Patchett A A, Arison B H, Ormond R E, Kuehl F A Jr, Albers-Schonberg G, Jardetzky O (1969) Phosphonomycin: structure and synthesis. Science 166:123-125.

Daley B J (2013) Peritonitis and abdominal sepsis. emedicine.medscape.com/article/180234-overview.

Demetri G D, Zenzie B W, Rheinwald J G, Griffin J D (1989) Expression of colony-stimulating factor genes by normal human mesothelial cells and human malignant mesothelioma cells lines in vitro. Blood 74:940-946.

Diederichs K, Jacques S, Boone T, Karplus P A (1991) Low-resolution structure of recombinant human granulocyte-macrophage colony stimulating factor. J Mol Biol 221:55-60.

Gennari R, Alexander J W, Gianotti L, Eaves-Pyles T, Hartmann S (1994) Granulocyte macrophage colony-stimulating factor improves survival in two models of gut-derived sepsis by improving gut barrier function and modulating bacterial clearance. Ann Surg 220:68-76.

Gobernado M (2003) Fosfomycin. Rev Esp Quimioter 16:15-40.

de Groot R P, Coffer P J, Koenderman L (1998) Regulation of proliferation, differentiation and survival by the IL-3/IL-5/GM-CSF receptor family. Cell Signal 10:619-628.

Hayashida K, Kitamura T, Gorman D M, Arai K, Yokota T, Miyajima A (1990) Molecular cloning of a second subunit of the receptor for human granulocyte-macrophage colony-stimulating factor (GM-CSF): reconstitution of a high-affinity GM-CSF receptor. Proc Natl Acad Sci USA 87:9655-9659.

Hendlin D, Stapley E O, Jackson M, Wallick H, Miller A K, Wolf F J, Miller T W, Chaiet L, Kahan F M, Foltz E L, Woodruff H B, Mata J M, Hernandez S, Mochales S (1969) Phosphonomycin, a new antibiotic produced by strains of *streptomyces*. Science 166:122-123.

Holzheimer R G (2001) Management of secondary peritonitis. In: Surgical Treatment: Evidence-Based and Problem-Oriented. Holzheimer R G, Mannick J A, editors. Munich: Zuckschwerdt.

Karageorgopoulos D E, Wang R, Yu X H, Falagas M E (2012) Fosfomycin: evaluation of the published evidence on the emergence of antimicrobial resistance in Gram-negative pathogens. J Antimicrob Chemother 67:255-268.

Kaushansky K, O'Hara P J, Berkner K, Segal G M, Hagen F S, Adamson J W (1986) Genomic cloning, characterization, and multilineage growth-promoting activity of human granulocyte-macrophage colony-stimulating factor. Proc Natl Acad Sci USA 83:3101-3105.

Kitamura T, Hayashida K, Sakamaki K, Yokota T, Arai K, Miyajima A (1991) Reconstitution of functional receptors for human granulocyte/macrophage colony-stimulating factor (GM-CSF): evidence that the protein encoded by the AIC2B cDNA is a subunit of the murine GM-CSF receptor. Proc Natl Acad Sci USA 88:5082-5086.

Lanfrancone L, Boraschi D, Ghiara P, Falini B, Grignani F, Peri G, Mantovani A, Pelicci P G (1992) Human peritoneal mesothelial cells produce many cytokines (granulocyte colony-stimulating factor [CSF], granulocyte-monocyte-CSF, macrophage-CSF, interleukin-1 [IL-1], and IL-6) and are activated and stimulated to grow by IL-1. Blood 80:2835-2842.

Lopez A F, Vadas M A, Woodcock J M, Milton S E, Lewis A, Elliott M J, Gillis D, Ireland R, Olwell E, Park L S (1991) Interleukin-5, interleukin-3, and granulocyte-macrophage colony-stimulating factor cross-compete for binding to cell surface receptors on human eosinophils. J Biol Chem 266:24741-24747.

Moonen P, Mermod J J, Ernst J F, Hirschi M, DeLamarter J F (1987) Increased biological activity of deglycosylated recombinant human granulocyte/macrophage colony-stimulating factor produced by yeast or animal cells. Proc Natl Acad Sci USA 84:4428-4431.

Orozco H, Arch J, Medina-Franco H, Pantoja J P, González Q H, Vilatoba M, Hinojosa C, Vargas-Vorackova F, Sifuentes-Osornio J (2006) Molgramostim (GM-CSF) associated with antibiotic treatment in nontraumatic abdominal sepsis: a randomized, double-blind, placebo-controlled clinical trial. Arch Surg 141:150-153.

Pachón-Ibáñez M E, Ribes S, Domínguez M A, Fernández R, Tubau F, Ariza J, Gudiol F, Cabellos C (2011) Efficacy of fosfomycin and its combination with linezolid, vancomycin and imipenem in an experimental peritonitis model caused by a *Staphylococcus aureus* strain with reduced susceptibility to vancomycin. Eur J Clin Microbiol Infect Dis 30:89-95.

Rodríguez A, Gallego A, Olay T, Mata J M (1977) Bacteriological evaluation of fosfomycin in clinical studies. Chemotherapy 23 Suppl 1:247-258.

Sato N, Sakamaki K, Terada N, Arai K, Miyajima A (1993) Signal transduction by the high-affinity GM-CSF receptor: two distinct cytoplasmic regions of the common beta subunit responsible for different signaling. EMBO J 12:4181-4189.

Schäfer K, Stöteknuel S, Schollmeyer P, Dobos G J (1998) Granulocyte macrophage-colony stimulating factor stimulates secretion of chemoattractive cytokines by peritoneal macrophages of CAPD patients. Adv Perit Dial 14:164-167.

Selgas R, Fernández de Castro M, Jiménez C, Cárcamo C, Contreras T, Bajo M A, Vara F, Corbí A (1996) Immunomodulation of peritoneal macrophages by granulocyte-macrophage colony-stimulating factor in humans. Kidney Int 50:2070-2078.

Shanafelt A B, Miyajima A, Kitamura T, Kastelein R A (1991a) The amino-terminal helix of GM-CSF and IL-5 governs high affinity binding to their receptors. EMBO J 10:4105-4112.

Shanafelt A B, Johnson K E, Kastelein R A (1991b) Identification of critical amino acid residues in human and mouse granulocyte-macrophage colony-stimulating factor and their involvement in species specificity. J Biol Chem 266:13804-13810.

Shinagawa N, Mizuno A, Mashita K, Yura J, Ishikawa S, Hirata K, Denno R, Mukaiya M, Ishibiki K, Aikawa N, et al (1994) [Bacteria isolated from intraabdominal infection and their susceptibilities to antimicrobial agents]. [Article in Japanese]. Jpn J Antibiot 47:1329-1343.

Shree N, Arora B S, Mohil R S, Kasana D, Biswal I (2013) Bacterial profile and patterns of antimicrobial drug resistance in intra-abdominal infections: Current experience in a teaching hospital. Indian J Pathol Microbiol 56:388-392.

Tobudic S, Matzneller P, Stoiser B, Wenisch J M, Zeitlinger M, Vychytil A, Jaeger W, Boehmdorfer M, Reznicek G, Burgmann H (2012) Pharmacokinetics of intraperitoneal and intravenous fosfomycin in automated peritoneal dialysis patients without peritonitis. Antimicrob Agents Chemother 56:3992-3995.

Toda H, Murata A, Oka Y, Uda K, Tanaka N, Ohashi I, Mori T, Matsuura N (1994) Effect of granulocyte-macrophage colony-stimulating factor on sepsis-induced organ injury in rats. Blood 83:2893-2898.

Troidle L, Finkelstein F (2006) Treatment and outcome of CPD-associated peritonitis. Ann Clin Microbiol Antimicrob 5:6.

Volk H D, Thieme M, Heym S, Döcke W D, Ruppe U, Tausch W, Manger D, Zuckermann S, Golosubow A, Nieter B, et al (1991) Alterations in function and phenotype of monocytes from patients with septic disease—predictive value and new therapeutic strategies. Behring Inst Mitt (88):208-215.

West R, Krag A, Gerbes A (2012) Spontaneous bacterial peritonitis. Gut 61:297-310.

Wong G G, Witek J S, Temple P A, Wilkens K M, Leary A C, Luxenberg D P, Jones S S, Brown E L, Kay R M, Orr E C, et al (1985) Human GM-CSF: molecular cloning of the complementary DNA and purification of the natural and recombinant proteins. Science 228:810-815.

The invention claimed is:

1. A method of inhibiting infectious peritonitis comprising a *Bacteroides fragilis* infection in a subject comprising: intraperitoneally administering to said subject a composition comprising active ingredients granulocyte-macrophage colony-stimulating factor (GM-CSF), fosfomycin, and metronidazole, in an amount sufficient to inhibit said infectious peritonitis comprising a *Bacteroides fragilis* infection, wherein the amount of each active ingredient is GM-CSF 25 micrograms to 100 micrograms, fosfomycin 2 grams to 8 grams, and metronidazole 500 milligrams to 2 grams.

2. The method according to claim 1, further comprising administering an additional antimicrobial or antibiotic agent active against bacteria of the *Bacteroides fragilis* group.

3. The method according to claim 2, wherein the additional antimicrobial or antibiotic agent comprises a carbapenem.

4. The method according to claim 2, wherein the additional antimicrobial or antibiotic agent comprises imipenem.

5. The method according to claim 2, wherein the additional antimicrobial or antibiotic agent comprises an antifungal agent.

6. The method according to claim 5, wherein the additional antifungal agent comprises fluconazole or caspofungin.

7. The method according to claim 1, further comprising administering a protease inhibitor suitable for in vivo administration into the peritoneal cavity.

8. The method according to claim 7, wherein the protease inhibitor suitable for in vivo administration into the peritoneal cavity comprises aprotinin or soybean trypsin inhibitor.

9. The method according to claim 1, wherein the composition has a pH of between 6.5 and 8.

10. The method according to claim 1, wherein the subject is a mammal.

11. The method according to claim 1, wherein the subject is a human.

12. The method according to claim 11, wherein the human is a child younger than 15 years of age.

13. The method according to claim 11, wherein the human is an adult of 15 years of age or older.

14. The method of claim 1, wherein the composition is an aqueous solution comprising GM-CSF at a concentration of 100 micrograms per liter, fosfomycin at a concentration of 8 grams per liter, metronidazole at a concentration of 2 grams per liter, and wherein a volume of the aqueous solution administered as a single dose is in the range of 250 milliliters to 1 liter.

15. The method of claim 1, wherein the amount of each active ingredient is GM-CSF 50 micrograms, fosfomycin 4 grams, and metronidazole 1 gram.

16. The method of claim 15, wherein the composition is an aqueous solution comprising GM-CSF at a concentration of 100 micrograms per liter, fosfomycin at a concentration of 8 grams per liter, metronidazole at a concentration of 2 grams per liter, and wherein the volume of the aqueous solution administered as a single dose is 500 milliliters.

17. The method of claim 1, wherein the GM-CSF is in the form of molgramostim.

* * * * *